US00PP21089P2

(12) United States Plant Patent
Deng et al.

(10) Patent No.: US PP21,089 P2
(45) Date of Patent: Jun. 22, 2010

(54) ***CALADIUM* PLANT NAMED '75-14'**
(50) Latin Name: *Caladium×hortulanum*
Varietal Denomination: 75-14

(75) Inventors: Zhanao Deng, Ellenton, FL (US); Brent Harbaugh, Bradenton, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/317,018

(22) Filed: Dec. 18, 2008

(51) Int. Cl.
*A01H 5/00* (2006.01)

(52) U.S. Cl. ..... Plt./373
(58) Field of Classification Search ..... Plt./373
See application file for complete search history.

*Primary Examiner*—Susan B McCormick Ewoldt

(57) ABSTRACT

A new *Caladium* plant named '75-14' particularly distinguished by its heart-shaped leaves with a white center, green margins, and numerous purple spots, and demonstrated potential to produce high tuber yield, develop attractive and sun-tolerant plants in outdoor sunny landscapes, and produce attractive pot plants when tubers are forced in containers, is disclosed.

2 Drawing Sheets

ACKNOWLEDGEMENT OF FEDERAL RESEARCH SUPPORT

This invention was made with government support under FLA-BRA-04162 awarded by the Cooperative State Research, Education, and Extension Service, USDA. The government has certain rights in the invention.

Genus and species: *Caladium×hortulanum.*

Variety denomination: '75-14'.

BACKGROUND OF THE NEW PLANT

The invention relates to a new and distinct variety of *Caladium×hortulanum* plant named '75-14'. '75-14' originated from a controlled pollination made in 2001 between 'Gingerland' (unpatented) and 'Florida Moonlight' (U.S. Plant Pat. No. 14,565). 'Gingerland' was selected as the seed parent because of its sun tolerance and bright leaf spots. 'Florida Moonlight' was used as the pollen parent for its high tuber yield, multiple branching habit, pure white leaf color, and heart shaped leaf. 'Florida Moonlight' was a progeny from the cross 'Aaron' (unpatented)×'Candidum Junior' (unpatented). The ancestry of 'Gingerland', 'Aaron', and 'Candidum Junior' are unknown, although 'Candidum Junior' was suspected to be a field mutation of 'Candidum' (unpatented). It was initially selected in 2002 as GCREC-1075-14. Asexual propagation of tubers and evaluation in field and pot studies since 2002 in Wimauma, Fla. have shown that the unique features of '75-14' are stable and reproduced true to type in successive generations of asexual propagation.

Plant Breeder's Rights for this cultivar have not been applied for. '75-14' has not been made publicly available more than one year prior to the filing of this application.

SUMMARY OF THE INVENTION

*Caladium* [*Caladium×hortulanum* Birdsey, Araceae Juss.] is commonly used as a pot or landscape plant and is valued for its colorful leaves. Commercial *caladium* plants are grown from tubers. The commercial value of a *caladium* cultivar depends on its tuber yield, leaf color, performance in the landscape as a garden plant, and performance in containers as a pot plant.

The new and distinct variety of *caladium* is a fancy-leaved *caladium*. It has a high potential for tuber production yield. Leaves possess a unique coloration: green-white near the center, dark green near the margin, and numerous purple spots. Plants are vigorous and develop numerous leaves that are resistant to sun burn. With these characteristics, '75-14' performs outstandingly in the landscape in full sun. '75-14' produces a uniquely colored plant of high quality when forced in containers.

DESCRIPTION OF THE PHOTOGRAPHS

This new *caladium* plant is illustrated by the accompanying photographs which show the plant's form and foliage. The new *caladium* has not been observed under all possible environmental conditions. Its phenotype may vary somewhat with variations in the environment such as light intensity and temperature, without, however, any variance in genotype. The colors shown are as true as can be reasonably obtained by conventional photographic procedures. Colors in the photograph may differ slightly from the color values cited in the detailed botanical description, which accurately describe the colors of the new *Caladium.*

DESCRIPTION OF THE NEW CULTIVAR

Figure 1:
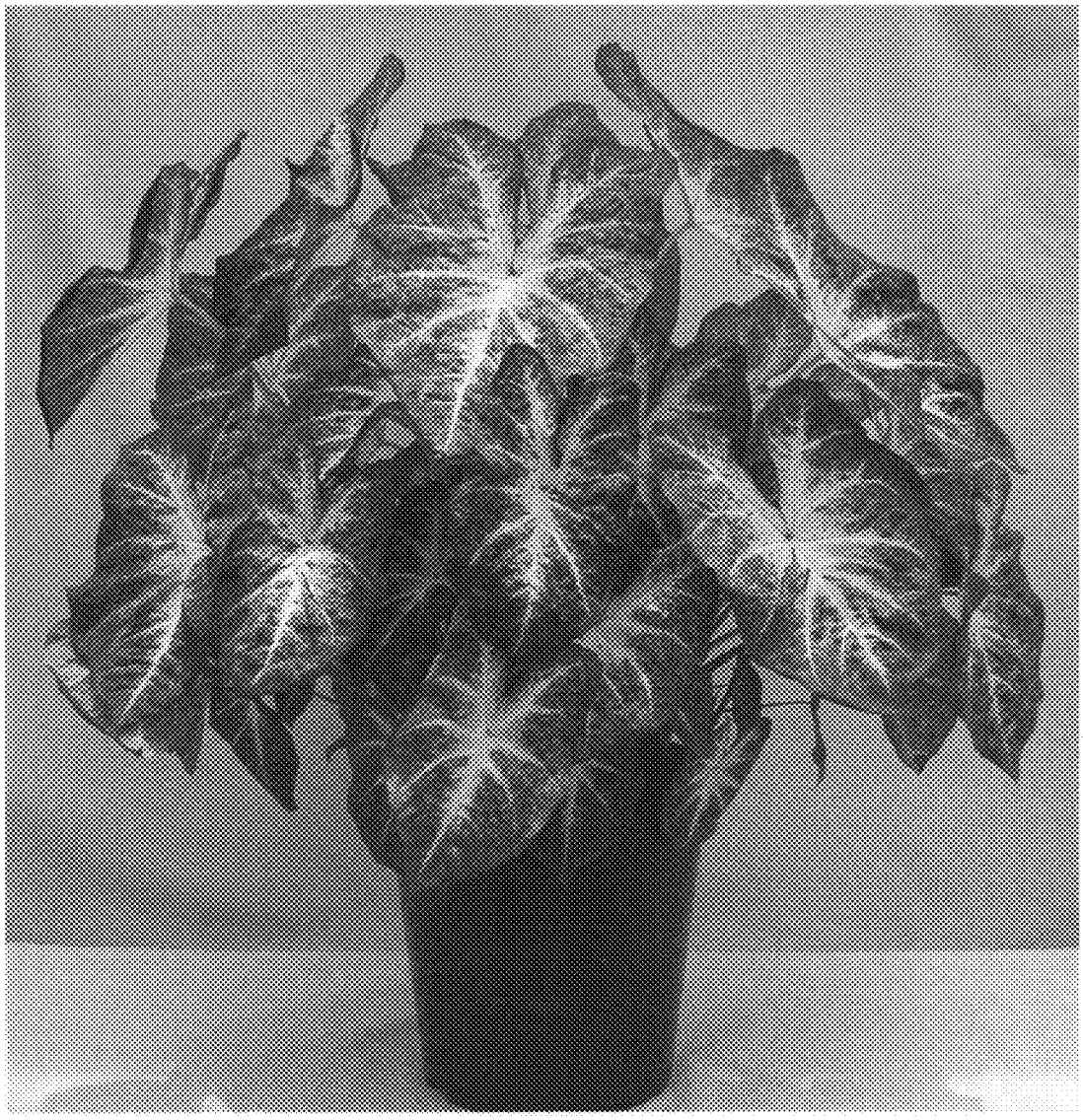
FIG. 1 shows the overall plant appearance and habit including foliage from a side perspective view of a typical plant of the new *Caladium* grown in a container.
Figure 2:
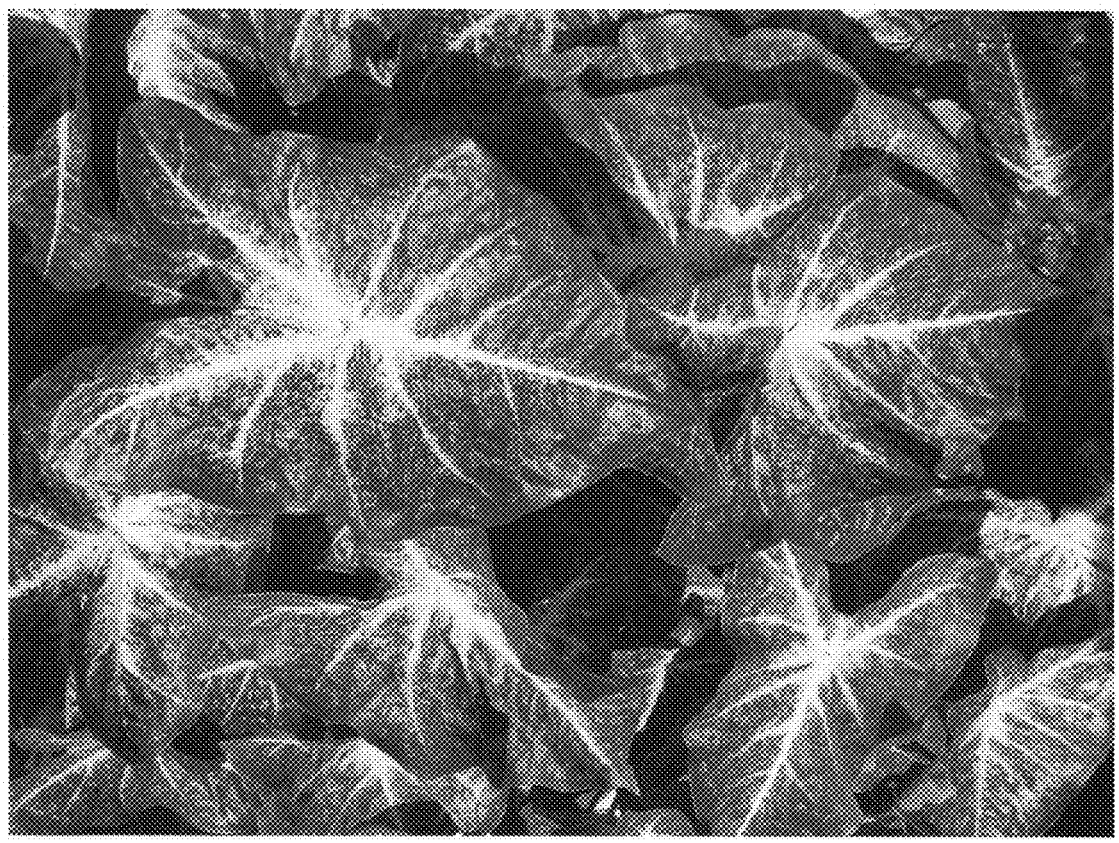
FIG. 2 shows a close-up of the foliage.

The following detailed description sets forth the distinctive characteristics of '75-14' with color terminology in accordance with British Color Council and The Royal Horticultural Society, Horticultural Colour Chart, except where general color terms of ordinary dictionary significance are obvious. Wherein dimensions, sizes, and other characteristics are given, it is to be understood that such characteristics are approximations of averages set forth as accurately as practicable. The description of the claimed plant is of four-month-old specimens grown in Wimauma, Fla., in 2005–2006. Plants used for describing color were grown in 11.4-cm containers in a 45% shaded greenhouse from No. 1 (3.8 to 6.4 cm in diameter) de-eyed tubers.

DETAILED BOTANICAL DESCRIPTION

Classification:

*Botanical.*—*Caladium×hortulanum.*

*Common name.*—*Caladium.*

Parentage:

*Female parent.*—'Gingerland' (unpatented) *caladium.*

*Male parent.*—'Florida Moonlight' (U.S. Plant Pat. No. 14,565) *caladium.*

Propagation:

*Type.*—By tuber division.

*Time to develop roots and sprout.*—37 days (Spring — 15° C. night to 29° C. day). 18 days (Summer — 21° C. night to 35° C. day).

*Root description.*—Dense, moderately thick roots (up to 2.5 mm at the basal end) with little branching and few lateral roots.

Plant description:

*Plant shape.*—Upright, symmetrical.

*Plant height.*—About 40 cm from top of soil to top of leaf plane 4 months from planting tubers in ground beds in full sun.

*Plant diameter.*—About 40–75 cm 4 months from planting tubers in ground beds in full sun.

*Leaf blade.*—Peltate, sagitate-cordate, with green-white (RHS 157A) palmate-pinnate venation. The upper surface has dark green (RHS 141A) margins, 2–3 mm wide, bordering the entire leaf except for the basal leaf valley where it is greyed-purple (RHS 185A). Interveinal areas are green-white (RHS 157A) near the central main vein and change to dark green (RHS 141A) near the margin. Leaves have a small red-purple blotch (1–3 mm diameter) at the petiole attachment and numerous (1 to 40 mm in diameter) greyed-purple (RHS 185B) spots. Netted green-white (RHS 157D) venation occurs on the leaf surface. The under-surface has a greyed-green (RHS 191B) margin, 2–3 mm wide. Primary veins are greyed-green (RHS 194B), and netted venation is greyed-green (RHS 191A). Interveinal areas are green-white (RHS 157A) near the central main and large veins and change to greyed-green (RHS 191A) near the margin. Greyed-purple spots (RHS 186A) are numerous and scattered between primary veins. The leaves are smooth and soft on both the upper and lower surface.

*Petiole.*—3–6 mm and light green (RHS 138D) at the apex, but the colors diffuse into a dark brown (RHS 200B) at the base that is around 5 to 9 mm in diameter. Length is 15–30 cm, with no wings present on the petiole.

*Tuber.*—Jumbo-sized (>6.4 cm and <8.9 cm in diameter) tubers are multi-segmented, bearing 5–6 dominant buds. Tuber surfaces are brown (RHS 200C) with the cortical area yellow-orange (RHS 15C).

*Flowers.*—Flowers have not been observed under natural growing conditions.

Resistance to insects, disease, or pests: No unusual resistance or susceptibility to insects, disease, or pests noted.

Temperature tolerance: Heat tolerant up to temperatures of 45° C. No unusual cold hardiness noted.

COMPARISON WITH KNOWN CULTIVARS

'75-14' was evaluated for tuber production and plant performance at the Gulf Coast Research and Education Center in Wimauma, Fla. in 2005 and 2006. The soil was an EauGallie fine sand with ~1% organic matter and pH of 6.2. Plants were grown on plastic-mulched raised-beds with a constant water table maintained using a seep irrigation system (Geraldson et. al, 1965). In 2005, ground beds were fumigated on February 25 (6 weeks before planting) with a mixture of 67% methyl bromide and 33% chloropicrin (by volume) at the rate of 392 kg·ha-1, and in 2006, the beds were fumigated on March 10, 10 days before planting, with the same fumigant mixture but at 196 kg·ha-1. The beds were 91 cm wide and 20 cm high with 2.54-cm *caladium* seed pieces (tuber pieces) planted 15 cm apart in three rows. Osmocote 18N-2.6P-10K 8–9 month controlled release fertilizer (Scotts Co., Marysville, Ohio) was applied to the bed surface when shoots were emerging from the soil with N at 336 kg·ha-1. Tubers were harvested in Nov. 2005 and Dec. 2006, respectively. Dried tubers were graded by their maximum diameter: No. 2 (>2.5 cm and <3.8 cm), No. 1 (>3.8 cm and <6.4 cm), Jumbo (>6.4 cm and <8.9 cm), Mammoth (>8.9 cm and <11.4 cm), and Super Mammoth (>11.4 cm). A production index (an indicator of economic value of the harvested tubers from each plot) was calculated: N (No. 2)+2N (No. 1)+4N (Jumbo)+6N (Mammoth)+8N (Super Mammoth), where N is the number of tubers in the grade.

Field plots were organized in a randomized complete block design consisting of three replications. Each plot was 1.2 m2 and was planted with 30 propagules (tuber pieces). Three major commercial cultivars that had the similar coloration pattern (spotted) were also planted in the field as controls to assess the tuber yield and plant performance of '75-14'. They were: 'Galaxy' (unpatented, fancy-leaved, vigorous), 'Gingerland' (lance-leaved, prostrate), and 'Miss Muffet' (unpatented, fancy-leaved, dwarf). An analysis of variance was conducted using the GLM procedure in the SAS program, followed by mean separation by Fisher's least square difference (LSD) (SAS Institute, 2003).

Compared to the controls, '75-14' was the most productive in 2005 (Table 1). Its tuber weight was 42%, 77%, and 160% greater than that of 'Galaxy', 'Gingerland', and 'Miss Muffet', respectively, and its production index was 51%, 25%, and 115% greater than that of the controls. '75-14' produced a similar number of marketable tubers with 'Gingerland', but '75-14' produced 69% or 56% more tubers than 'Galaxy' and 'Miss Muffet'. In 2006, '75-14' was also more productive than 'Gingerland' and 'Miss Muffet': tuber weight 48% or 220% greater, production index 41% or 126% greater, and number of marketable tubers 78% or 81% greater than that of 'Gingerland' and 'Miss Muffet', respectively. Tuber weight of '75-14' in 2006 was 27% less than that of 'Galaxy', but '75-14' produced 18% more marketable tubers than 'Galaxy' and both had the same production index. As much as 80 to 90% of the marketable tubers produced by '75-14' were in the No. 1, Jumbo, Mammoth, and even Super Mammoth categories.

Landscape performance of '75-14' grown under full-sun conditions was evaluated in 2005 and 2006 on the same plots used for assessing tuber production. Plant height, number of leaves, and leaf sizes were recorded approximately 4 months after planting. Three plants in the center of each plot (with 30 plants) were randomly selected for the objective measurements. Plants in the each plot were also evaluated for overall plant quality and leaf sun bum tolerance, three times in the 2005 growing season and two times in the 2006 growing season. The scale for plant quality evaluation was 1 to 5: with 1 being very poor (few leaves and lack of vigor), and 5 being excellent (full plants, numerous leaves, and bright color display), and the scale for leaf sun burn tolerance was also 1 to 5, with 1 being very susceptible to sun burn (leaves having numerous sun-damaged areas or holes) and 5 being resistant to sun burn (no visible sun-damaged areas).

'75-14' plants were about 10 cm taller than 'Galaxy' and 'Gingerland', and 26 cm taller than 'Miss Muffet'. The leaves of '75-14' were smaller than those of 'Galaxy' and 'Gingerland' but slightly larger than those of 'Miss Muffet' (Table 2). For overall plant quality, '75-14' received the highest scores among the cultivars tested in both growing seasons (2005 and 2006) and its scores were significantly higher than all controls in three of the five evaluations. The leaf sun tolerance of '75-14' was rated 4 to 5 (good to very good) in all the evaluations during the two growing seasons. Except for one evaluation in Sep. 2006, '75-14's sun tolerance ratings were higher than all controls.

'75-14's performance in container forcing was evaluated by planting No. 1 4-cm containers. Dry tubers were planted either intact or de-eyed in a peat/vermiculite mix (VerGro Container Mix A, Verlite, Tampa, Fla.) on Mar. 26, 2007. The tests were performed in a greenhouse with 45% light exclusion during the summer in Wimauma, Fla. Average daily temperatures ranged from a low of 16° C. (night) to a high of 29° C. (day) during the tests. Plants were grown on metal benches in the greenhouse and arranged according to a randomized complete block design with 10 replications. Three fancy-leaved commercial cultivars, 'Candidum Junior' (a cultivar commonly used for pot plant production), 'Galaxy', and 'Miss Muffet' were included as controls. Plant height, number of leaves, and leaf sizes were recorded 8 weeks after planting. At the same time, each pot plant was rated on a scale of 1 to 5 for quality as pot plants: 1=very poor, 3=fair and 5=very good (many leaves, bright and full plants). An analysis of variance and mean separation were done using the GLM procedure in the SAS program to compare the performance of '75-14' to the controls.

'75-14' sprouted in 37 days (intact or de-eyed) after planting, similar to 'Galaxy', but 3–6 days later than 'Candidum Junior' and 7–10 days later than 'Miss Muffet' and (Table 3). '75-14' plants were 27 cm (intact tubers) or 25 cm (de-eyed tubers) tall, similar to 'Galaxy' in height, but were significantly taller than 'Candidum Junior' (8–10 cm taller) and 'Miss Muffet' (a known dwarf cultivar) (10 to 12 cm taller). '75-14' had 7 leaves on intact plants 8 weeks after planting, similar to 'Galaxy', but less than 'Canadium Junior' or 'Miss Muffet' plants, although the difference was not statistically significant. When tubers were de-eyed, '75-14' produced averaged 6 more leaves (13 per plant) than plants grown from intact tubers. In leaf size (length and width), '75-14' was similar to 'Galaxy' and 'Candidum Junior'. Tuber de-eyeing significantly improved the quality rating of the pot plants, from 3.3 to 4.2. This indicates that '75-14' can be used for forcing in small containers, but tuber de-eyeing will be required to produce high quality plants.

TABLE 1

Tuber weights, production index, and tuber grade distribution of '75-14' and three commercial cultivars (controls) harvested in 2005 and 2006. Values presented are means of three replications with 30 propagules per 1.2-m$^2$ plot per year.

| | Tuber | | |
|---|---|---|---|
| | Weight (kg) | Production index | Marketable (number) |
| | Year 2005 | | |
| 75-14 | 8.2 | 247 | 58 |
| Galaxy | 5.8 | 163 | 34 |
| Gingerland | 4.6 | 197 | 59 |
| Miss Muffet | 3.2 | 115 | 37 |
| | Year 2006 | | |
| 75-14 | 8.6 | 240 | 70 |
| Galaxy | 11.9 | 240 | 59 |
| Gingerland | 5.8 | 170 | 39 |
| Miss Muffet | 2.7 | 106 | 39 |

TABLE 1-continued

Tuber weights, production index, and tuber grade distribution of '75-14' and three commercial cultivars (controls) harvested in 2005 and 2006. Values presented are means of three replications with 30 propagules per 1.2-m$^2$ plot per year.

| | Tuber distribution (%) | | | | |
|---|---|---|---|---|---|
| Cultivar | Super mammoth | Mammoth | Jumbo | No. 1 | No. 2 |
| | Year 2005 | | | | |
| 75-14 | 14 | 22 | 30 | 26 | 5 |
| Galaxy | 10 | 32 | 45 | 9 | 4 |
| Gingerland | 0 | 18 | 37 | 30 | 14 |
| Miss Muffet | 0 | 11 | 39 | 40 | 11 |
| | Year 2006 | | | | |
| 75-14 | 5 | 26 | 16 | 32 | 21 |
| Galaxy | 15 | 21 | 26 | 17 | 21 |
| Gingerland | 13 | 32 | 20 | 23 | 13 |
| Miss Muffet | 0 | 9 | 29 | 41 | 21 |

The production index is an indicator of economic value of the crop harvested and is calculated as: N (No. 2s) + 2N (No. 1s) + 4N (Jumbos) + 6N (Mammoth) + 8N (Super Mammoth); where N = number of tubers in each grade. Tuber distribution data (%) were transformed using the formula arcsine [square root (percentage/100)] before analysis of variance and mean separation. Tubers graded by maximum diameter; No. 2 (2.5 to 3.8 cm), No. 1 (3.8 to 6.4 cm), Jumbo (6.4 to 8.9 cm), Mammoth (8.9 to 11.4 cm), and Super Mammoth >11.4 cm).

TABLE 2

Plant and leaf measurements, plant performance ratings, and sun burn tolerance ratings of '75-14' and three commercial cultivars grown in ground beds in full sun (2005 and 2006).

| Cultivar | Plant ht (cm) | Leaves (no.) | Leaf length (cm) | Leaf width (cm) |
|---|---|---|---|---|
| 75-14 | 40 | 40 | 19.7 | 12.4 |
| Galaxy | 30 | 40 | 22.7 | 15.2 |
| Gingerland | 31 | 25 | 26.7 | 14.6 |
| Miss Muffet | 14 | 19 | 16.3 | 10.0 |

| | Plant performance rating[z] | | | | |
|---|---|---|---|---|---|
| Cultivar | June 2005 | July 2005 | August 2005 | August 2006 | September 2006 |
| 75-14 | 4.5 | 4.9 | 4.8 | 3.7 | 3.7 |
| Galaxy | 3.6 | 4.1 | 4.5 | 1.8 | 2.9 |
| Gingerland | 1.8 | 3.4 | 4.0 | 1.7 | 2.8 |
| Miss Muffet | 1.5 | 1.3 | 2.4 | 1.3 | 1.5 |

| | Sun tolerance rating[y] | | | | |
|---|---|---|---|---|---|
| Cultivar | May 2005 | July 2005 | August 2005 | August 2006 | September 2006 |
| 75-14 | 4.6 | 5.0 | 4.7 | 4.5 | 4.1 |
| Galaxy | 4.2 | 4.6 | 4.3 | 3.8 | 4.3 |
| Gingerland | 4.1 | 4.7 | 4.4 | 4.3 | 4.5 |
| Miss Muffet | 3.5 | 4.4 | 4.2 | 4.3 | 4.2 |

[z]Plants were rated on a scale of 1 to 5, with 1 being very poor, 3 fair and acceptable, and 5 being excellent in plant vigor, fullness and color display, in June, July, and August 2005, and August and September 2006, respectively.
[y]Plants' sun burn tolerance was rated on a scale of 1 to 5, with 1 being very poor, 3 fair and acceptable, and 5 being excellent without showing any signs of leaf burns or resulting holes on leaf surfaces, taken in June, July, and August 2005, and August and September 2006, respectively.

TABLE 3

Plant performance for *caladium* cultivars grown from No. 1 tubers in 11.4-cm containers in a 45% shaded glasshouse, 2007, Wimauma, Fla. Values represent the means of plants producted from 8 intact or 10 de-eyed No. 1 (>3.8 and <6.4 cm in diameter) tubers planted individually per container.

| | Days to sprout[z] | | Plant ht (cm) | | Leaves (no.) | |
|---|---|---|---|---|---|---|
| Cultivar | Intact | De-eye | Intact | De-eye | Intact | De-eye |
| 75-14 | 37 | 37 | 27 | 25 | 7 | 13 |
| Candidum Junior | 31 | 34 | 19 | 15 | 11 | 10 |
| Galaxy | 33 | 36 | 26 | 25 | 7 | 9 |
| Miss Muffet | 27 | 30 | 15 | 15 | 9 | 18 |

TABLE 3-continued

Plant performance for *caladium* cultivars grown from No. 1 tubers in 11.4-cm containers in a 45% shaded glasshouse, 2007, Wimauma, Fla. Values represent the means of plants producted from 8 intact or 10 de-eyed No. 1 (>3.8 and <6.4 cm in diameter) tubers planted individually per container.

| | Leaf length (cm) | | Leaf width (cm) | | Quality rating | |
|---|---|---|---|---|---|---|
| Cultivar | Intact | De-eye | Intact | De-eye | Intact | De-eye |
| 75-14 | 18.1 | 18.0 | 12.2 | 11.4 | 3.3 | 4.2 |
| Candidum Junior | 20.4 | 18.4 | 13.2 | 11.2 | 3.6 | 3.5 |
| Galaxy | 22.3 | 18.4 | 14.6 | 12.2 | 2.3 | 3.3 |
| Miss Muffet | 19.4 | 15.4 | 12.5 | 8.6 | 3.1 | 4.4 |

[z]Number of days from planting to the first unfurled leaf.

I claim:

1. A new and distinct cultivar of *Caladium* plant as shown and described herein.

* * * * *